(12) United States Patent
Uchiyama et al.

(10) Patent No.: US 8,025,844 B2
(45) Date of Patent: Sep. 27, 2011

(54) HYDROGEN SENSOR AND HYDROGEN GAS DETECTING APPARATUS

(75) Inventors: Naoki Uchiyama, Hamamatsu (JP); Naoki Matsuda, Miyaki-gun (JP); Kazuki Yoshimura, Ichinomiya (JP); Kenji Kato, Abiko (JP)

(73) Assignees: Kabushiki Kaisha Atsumitec (JP); National Institute of Advanced Industrial Science and Technology (JP)

( * ) Notice: Subject to any disclaimer, the term of this patent is extended or adjusted under 35 U.S.C. 154(b) by 310 days.

(21) Appl. No.: 12/515,950

(22) PCT Filed: Jul. 10, 2007

(86) PCT No.: PCT/JP2007/063744
§ 371 (c)(1),
(2), (4) Date: May 21, 2009

(87) PCT Pub. No.: WO2008/062582
PCT Pub. Date: May 29, 2008

(65) Prior Publication Data
US 2010/0054999 A1   Mar. 4, 2010

(30) Foreign Application Priority Data

Nov. 22, 2006 (JP) .................................. 2006-315600

(51) Int. Cl.
*G01N 17/00* (2006.01)
*G01N 7/00* (2006.01)
*G01N 21/00* (2006.01)
*G01N 27/00* (2006.01)
*G01N 31/00* (2006.01)
*G01N 33/00* (2006.01)

(52) U.S. Cl. ............ 422/91; 422/50; 422/401; 422/402; 422/83; 422/85; 436/144; 436/164; 436/171; 73/1.02

(58) Field of Classification Search .................... 422/50, 422/401, 402, 83, 85, 91; 436/144, 164, 436/171; 73/1.02
See application file for complete search history.

(56) References Cited

U.S. PATENT DOCUMENTS
4,661,320 A   4/1987   Ito et al.
(Continued)

FOREIGN PATENT DOCUMENTS
JP   58-79141 A   5/1983
(Continued)

OTHER PUBLICATIONS
International Search Report dated Aug. 7, 2007, issued in corresponding PCT/JP2007/063744.
(Continued)

*Primary Examiner* — Brian J Sines
(74) *Attorney, Agent, or Firm* — Rossi, Kimms & McDowell LLP

(57) ABSTRACT

A hydrogen sensor includes a thin film layer formed on a top surface of a planar optical transmission medium, and a catalyst layer formed on a top surface of the thin film layer. A first interface is created between the planar optical transmission medium and the thin film layer. A substrate is joined to a bottom surface of the planar optical transmission medium so that a second interface is created between the planar optical transmission medium and the substrate. On entering a first end portion of the planer optical transmission medium, light from a light source is spread by an entrance section, and the spread light is transmitted inside the planar optical transmission medium to a second end portion by being reflected by the first and second interfaces alternately. Light exiting from the second end portion is transmitted to an optical sensor by an exit light-collecting section. If the thin film layer is hydrogenated by the catalyst layer contacted by hydrogen, the amount of light reflected from the first interface reduces. Hydrogen gas is detected by the optical sensor detecting such reduction in the amount of light.

12 Claims, 7 Drawing Sheets

U.S. PATENT DOCUMENTS

| | | | |
|---|---|---|---|
| 6,903,815 B2 * | 6/2005 | Uchiyama et al. | 356/305 |
| 7,054,514 B2 * | 5/2006 | Uchiyama et al. | 385/12 |
| 2004/0173004 A1 * | 9/2004 | Eblen et al. | 73/31.05 |
| 2005/0186117 A1 * | 8/2005 | Uchiyama et al. | 422/91 |

FOREIGN PATENT DOCUMENTS

| | | |
|---|---|---|
| JP | 60-39536 A | 3/1985 |
| JP | 4-351948 A | 12/1992 |
| JP | 7-72081 A | 3/1995 |
| JP | 7-243973 A | 9/1995 |
| JP | 8-75639 A | 3/1996 |
| JP | 11-106384 A | 4/1999 |
| JP | 2005-83832 A | 3/2005 |
| JP | 2007-33203 A | 2/2007 |
| JP | 2007-101471 A | 4/2007 |

OTHER PUBLICATIONS

Written Opinion of the International Searching Authority dated Aug. 7, 2007, issued in corresponding PCT/JP2007/063744.

* cited by examiner

HYDROGEN SENSOR AND HYDROGEN GAS DETECTING APPARATUS

This is a U.S. National Phase Application of PCT International Application PCT/JP2007/063744 (published as WO 2008/062582) having an international filing date of Jul. 10, 2007, which is based on and claims priority from JP 2006-315600 filed on Nov. 22, 2006, the contents of each of which are incorporated herein in their entirety by reference.

TECHNICAL FIELD

This invention relates to a hydrogen sensor and a hydrogen gas detecting apparatus for detecting hydrogen gas.

BACKGROUND ART

Hydrogen has been attracting attention as an energy source enabling reduction of carbon dioxide emissions. There is, however, a risk of explosion of hydrogen gas that has leaked into an atmosphere (around a hydrogen gas production apparatus or a hydrogen gas storage apparatus, in a car park for hydrogen-fueled vehicles, etc., for example). Thus, it is necessary to quickly detect a hydrogen gas leak and stop it.

In this connection, hydrogen sensors for detecting hydrogen gas have been developed, one of which is shown in Japanese Unexamined Patent Publication No. 2005-083832 (Patent Document 1), for example. As shown in FIG. 8, this hydrogen sensor 10' has a light control film (reflecting film) 14 consisting of a thin film layer 12 and a catalyst layer 13, formed on a top surface of a light-transmitting member 11 of glass or the like. At normal temperature, when contacted by hydrogen gas in an atmosphere, the catalyst layer 13 quickly causes reversible hydrogenation of the thin film layer 12, thereby causing a change in optical reflectance of the thin film layer 12.

FIG. 9 shows a schematic structure of a hydrogen gas detecting apparatus 20' using such hydrogen sensor 10'. As shown in FIG. 9, in the hydrogen gas detecting apparatus 20', light 21a from a light source 21 is reflected by the light control film 14 of the hydrogen sensor 10', and the reflected light is received by an optical sensor 22. A hydrogen gas leak can be detected from a change in the amount of reflected light received by the optical sensor 22.

In this hydrogen gas detecting apparatus 20', light 21a from the light source 21 travels in the atmosphere and arrives at the optical sensor 22. Thus, there is a possibility that light from a light source other than the light source 21 (disturbance light from an illumination lamp at the ceiling of an underground car park, a headlight of a vehicle or the like, for example) is received by the optical sensor 22, or undergoes reflection or the like at the hydrogen sensor 10' and is received by the optical sensor 22. There is also a possibility that suspended dust in the optical path from the light source 21 to the hydrogen sensor 10' or in the optical path from the hydrogen sensor 10' to the optical sensor 22 prevents the optical sensor 22 from receiving light. There is also a possibility that dust or the like covers the hydrogen sensor 10' and prevents the optical sensor 22 from receiving light.

The hydrogen gas detecting apparatus 20' detects a change in transmittance caused by hydrogenation only in a narrow area (almost a point) of the hydrogen sensor on which light 21a is thrown. Thus, the hydrogen gas detecting apparatus 20' has room for improvement in hydrogen gas sensitivity.

DISCLOSURE OF THE INVENTION

The present invention has been made in view of the problems mentioned above. An object of the present invention is to provide a hydrogen sensor and a hydrogen gas detecting apparatus which can detect hydrogen gas without being affected by disturbance light, dust in the atmosphere or the like. Another object of the present invention is to provide a hydrogen sensor and a hydrogen gas detecting apparatus which have high hydrogen-gas sensitivity and can provide improved reliability of hydrogen gas detection. Preferably, another object of the present invention is to provide a hydrogen sensor and a hydrogen gas detecting apparatus which allows optional setting of time taken for detection of hydrogen gas.

In order to achieve the above objects, a hydrogen sensor according to the present invention comprises a planar optical transmission medium, a thin film layer formed on a top surface of the planar optical transmission medium, a catalyst layer formed on a top surface of the thin film layer, a substrate joined to a bottom surface of the planar optical transmission medium, an entrance section for introducing light emitted from a light source into a first end portion of the planer optical transmission medium, and an exit light-collecting section for collecting light that exits from a second end portion of the planar optical transmission medium and transmitting it to an optical sensor. A first interface is created between the planar optical transmission medium and the thin film layer, and a second interface is created between the planar optical transmission medium and the substrate.

Thus, light introduced into the first end portion of the planar optical transmission medium is transmitted inside the planar optical transmission medium to the second end portion, by being reflected by the first and second interfaces alternately. The light transmitted to the second end portion in this manner exits the planar optical transmission medium and is collected by the exit light-collecting section to be transmitted to the optical sensor.

Here, when contacted by hydrogen gas, the catalyst layer hydrogenates the thin film layer, thereby reversibly reducing the optical reflectance (hereinafter referred to simply as "reflectance") of the thin film layer and the first interface. Thus, the reflectance of the thin film layer and the first interface is reduced, so that the transmittance of the thin film layer and the first interface is increased in the vicinity of the catalyst layer contacted by hydrogen gas. Consequently, part or almost all of incoming light passes through the thin film layer to the catalyst layer, thus leaks from the planer optical transmission medium, so that the amount of light entering the exit light-collecting section reduces. On the basis of such reduction in the amount of light, the hydrogen sensor can detect hydrogen gas.

In this way, the hydrogen sensor detects hydrogen gas on the basis of a reduction in the amount of light that is transmitted inside the planer optical transmission medium in a manner that it is reflected by the first and second interfaces, and therefore the hydrogen sensor can detect hydrogen gas without being affected by disturbance light, dust in the atmosphere or the like.

When the hydrogen sensor includes means for spreading light in the direction of thickness of the planar optical transmission medium and introducing the light into the planar optical transmission medium, the spread light is transmitted inside the planar optical transmission medium to the second end portion by being reflected by the first and second interfaces alternately and exists from the second end portion, where the reflection by the first interface occurs on a line extending in the direction of length of the planar optical transmission medium. The light spread in the direction of thickness of the planar optical transmission medium when it exits from the second end portion, but the light is collected by the exit light-collecting section on its exiting from the second end portion, and transmitted to the optical sensor. The hydrogen sensor configured this way can transmit a change in reflectance of the thin film layer that has occurred in any part of the aforementioned line to the optical sensor, through a reduction in the amount of outgoing light, thus enabling hydrogen gas detection with high sensitivity and improved reliability.

When, on the other hand, the hydrogen sensor includes means for spreading light in the direction of width of the planar optical transmission medium and introducing the light into the planar optical transmission medium, the spread light is transmitted inside the planar optical transmission medium to the second end portion by being reflected by the first and second interfaces alternately and exits from the second end portion, where the reflection by the first interface occurs on lines located at equal intervals in the direction of length of the planar optical transmission medium. The light spread in the direction of width of the planar optical transmission medium when it exits from the second end portion, but the light is collected by the exit light-collecting section on its exiting from the second end portion, and transmitted to the optical sensor. The hydrogen sensor configured this way can transmit a change in reflectance of the thin film layer that has occurred in any part of any of the aforementioned lines to the optical sensor, through a reduction in the amount of outgoing light, thus enabling hydrogen gas detection with high sensitivity and improved reliability.

When the hydrogen sensor includes both means for spreading light in the direction of thickness of the planar optical transmission medium and introducing the light into the planar optical transmission medium and means for spreading light in the direction of width of the planar optical transmission medium and introducing light into the planar optical transmission medium, the spread light is transmitted inside the planar optical transmission medium to the second end portion by being reflected by the first and second interfaces alternately and exists from the second end portion, where the reflection by the first interface occurs on a plane extending in the directions of length and width of the planar optical transmission medium. The hydrogen sensor configured this way can transmit a change in reflectance of the thin film layer that has occurred in any part of the aforementioned plane to the optical sensor, through a reduction in the amount of outgoing light, thus enabling hydrogen gas detection with high sensitivity and improved reliability.

To sum up, the hydrogen sensor according to the present invention has means for spreading the light emitted from the light source in the direction of thickness of the planar optical transmission medium and introducing the light into the planar optical transmission medium and/or means for spreading the light emitted from the light source in the direction of width of the planar optical transmission medium and introducing the light into the planar optical transmission medium, which enables hydrogen gas detection with high sensitivity and improved reliability.

Preferably, in the hydrogen sensor according to the present invention, the planar optical transmission medium and the substrate constitute a slab optical waveguide allowing light to enter and exit at an angle not limited to a specific angle. This configuration advantageously spread light in either or both of the thickness and width directions of the planar optical transmission medium on its entering the planar optical transmission medium.

Preferably, in the hydrogen sensor according to the present invention, the substrate has a reflective film formed on a top surface thereof and is joined to the bottom surface of the planar optical transmission medium with the reflective film interposed therebetween so that the second interface is created between the planar optical transmission medium and a top surface of the reflective film.

In this configuration, light is reflected by the second interface created between the planar optical transmission medium and the top surface of the reflective film, and therefore stable reflection by the second interface can be secured. By restraining irregular reflection at the second interface in this manner, light accurately representing a change in reflectance at the first interface can be transmitted to the optical sensor, which leads to improved accuracy of hydrogen gas detection.

Preferably, in the hydrogen sensor according to the present invention, the reflective film is formed of nickel. In this case, the reflection of light by the second interface is substantially total internal reflection, and therefore more stable reflection by the second interface can be secured, which leads to further improved accuracy of hydrogen gas detection. Further, the reflective film of nickel serves as an oxidation protection layer for the thin film layer and catalyst layer, which leads to improved reliability and durability of the hydrogen sensor.

Preferably, in the hydrogen sensor according to the present invention, when the catalyst layer contacted by hydrogen gas hydrogenates the thin film layer, the thin film layer changes from a specular reflection state causing specular reflection of incoming light at the first interface, to an absorption state absorbing the incoming light in its region near the first interface, and then to a transmission state transmitting the incoming light to the catalyst layer. Time taken for the transition of the thin film layer from the specular reflection state to the transmission state depends on a wavelength of incoming light on the first interface.

Thus, the hydrogen sensor configured this way allows appropriate setting of time taken for the transition of the thin film layer from the specular reflection state to the transmission state, by selecting a wavelength of outgoing light from the exit light-collecting section, and therefore allows setting of time taken for detection of hydrogen gas present in the atmosphere, for example hydrogen gas that has leaked into the atmosphere.

Preferably, in the hydrogen sensor according to the present invention, the catalyst layer is formed of palladium and the thin film layer is formed of magnesium-nickel alloy. Configuring a hydrogen sensor in this manner, it is possible to realize a hydrogen sensor in which the thin film layer is capable of transition from the specular reflection state to the absorption state, and then to the transmission state, and in which time taken for this state transition depends on a wavelength of incoming light on the first interface.

In order to achieve the aforementioned objects, in a hydrogen gas detecting apparatus according to the present invention which is designed to detect hydrogen gas in an atmosphere by introducing light emitted from a light source into a hydrogen sensor and then detecting light exiting the hydrogen sensor by an optical sensor, the hydrogen sensor is configured as described above. Accordingly, it is possible to realize a hydrogen gas detecting apparatus, in which influence of disturbance light, dust in the atmosphere or the like can be excluded, and which has high hydrogen-gas sensitivity.

Preferably, in the hydrogen gas detecting apparatus according to the present invention, the planar optical transmission medium and the substrate of the hydrogen sensor constitute a slab optical waveguide allowing light to enter and exit at an angle not limited to a specific angle. As mentioned above, this configuration advantageously spread light in either or both of the thickness and width directions of the planar optical transmission medium on its entering the planar optical transmission medium.

Preferably, in the hydrogen gas detecting apparatus according to the present invention, the substrate of the hydrogen sensor has a reflective film formed on a top surface thereof and is joined to the bottom surface of the planar optical transmission medium with the reflective film interposed therebetween so that the second interface is created between the planar optical transmission medium and a top surface of the reflective film.

In this configuration, light is reflected by the second interface created between the planar optical transmission medium and the top surface of the reflective film, and therefore stable reflection by the second interface can be secured. By restraining irregular reflection at the second interface in this manner, light accurately representing a change in reflectance at the first interface can be transmitted to the optical sensor, which leads to improved accuracy of hydrogen gas detection.

Preferably, in the hydrogen gas detecting apparatus according to the present invention, the reflective film is formed of nickel. In this case, the reflection of light by the second interface is substantially total internal reflection, and therefore more stable reflection by the second interface can be secured, which leads to further improved accuracy of hydrogen gas detection. Further, the reflective film of nickel serves as an oxidation protection layer for the thin film layer and catalyst layer, which leads to improved reliability and durability of the hydrogen sensor.

Preferably, in the hydrogen gas detecting apparatus according to the present invention, the thin film layer of the hydrogen sensor is capable of the above-described transition from a specular reflection state to an absorption state, and then to a transmission state, and time taken for the transition from the specular reflection state to the transmission state depends on a wavelength of incoming light on the first interface. This hydrogen gas detecting apparatus includes a light source for emitting light to the entrance section of the hydrogen sensor and an optical sensor for receiving light transmitted from the exit section of the hydrogen sensor, and detects hydrogen gas by comparing the amount of the light received by the optical sensor with a threshold value set in advance. This hydrogen gas detecting apparatus further comprises at least one of means for changing wavelength distribution of light emitted from the light source, a color filter disposed on an optical path from the light source to the optical sensor and an optical sensor that is configured, as the aforementioned optical sensor, with a photoelectric transducer having a wavelength-dependent photoelectric conversion characteristic.

When the hydrogen gas detecting apparatus has means for changing wavelength distribution of light emitted from the light source, it is possible to select light having a wavelength for which the state transition of the thin film layer is fast or light having a wavelength for which the state transition of the thin film layer is slow, by changing the wavelength distribution of light emitted from the light source.

When the hydrogen gas detecting apparatus has a color filter, it is possible to select light having a wavelength for which the state transition of the thin film layer is fast or light having a wavelength for which the state transition of the thin film layer is slow, by changing the wavelength distribution of light received by the optical sensor. It is also possible to select light having a wavelength for which the state transition of the thin film layer is fast or light having a wavelength for which the state transition of the thin film layer is relatively slow, from the light exiting the hydrogen sensor.

When the hydrogen gas detecting apparatus has an optical sensor that is configured with a photoelectric transducer having a wavelength-dependent photoelectric conversion characteristic, it is possible to select light having a wavelength for which the state transition of the thin film layer is fast or light having a wavelength for which the state transition of the thin film layer is relatively slow, from the light exiting the hydrogen sensor.

Thus, in this hydrogen gas detecting apparatus, time taken for detection of a reduction in the amount of light exiting the hydrogen sensor, that is, time taken for detection of hydrogen gas present in the atmosphere, for example hydrogen gas that has leaked into the atmosphere can be set optionally, by selecting a wavelength of light to be received by the optical sensor in the above-described manners and then comparing the amount of light received by the optical sensor with a threshold value optionally set in advance.

Preferably, in the hydrogen gas detecting apparatus according to the present invention, the catalyst layer of the hydrogen sensor is formed of palladium and the thin film layer is formed of magnesium-nickel alloy. By configuring a hydrogen gas detecting apparatus in this manner, it is possible to realize a hydrogen gas detecting apparatus having a hydrogen sensor in which the thin film layer is capable of the above-described transition from a specular reflection state to an absorption state, and then to a transmission state, and in which time taken for this state transition depends on a wavelength of incoming light on the first interface.

As stated above, the hydrogen sensor and the hydrogen gas detecting apparatus according to the present invention can exclude the influence of disturbance light, dust in the atmosphere or the like. Further, the hydrogen sensor and the hydrogen gas detecting apparatus according to the present invention can detect hydrogen gas with high sensitivity and improved reliability.

BEST MODE OF CARRYING OUT THE INVENTION

Figure 1:
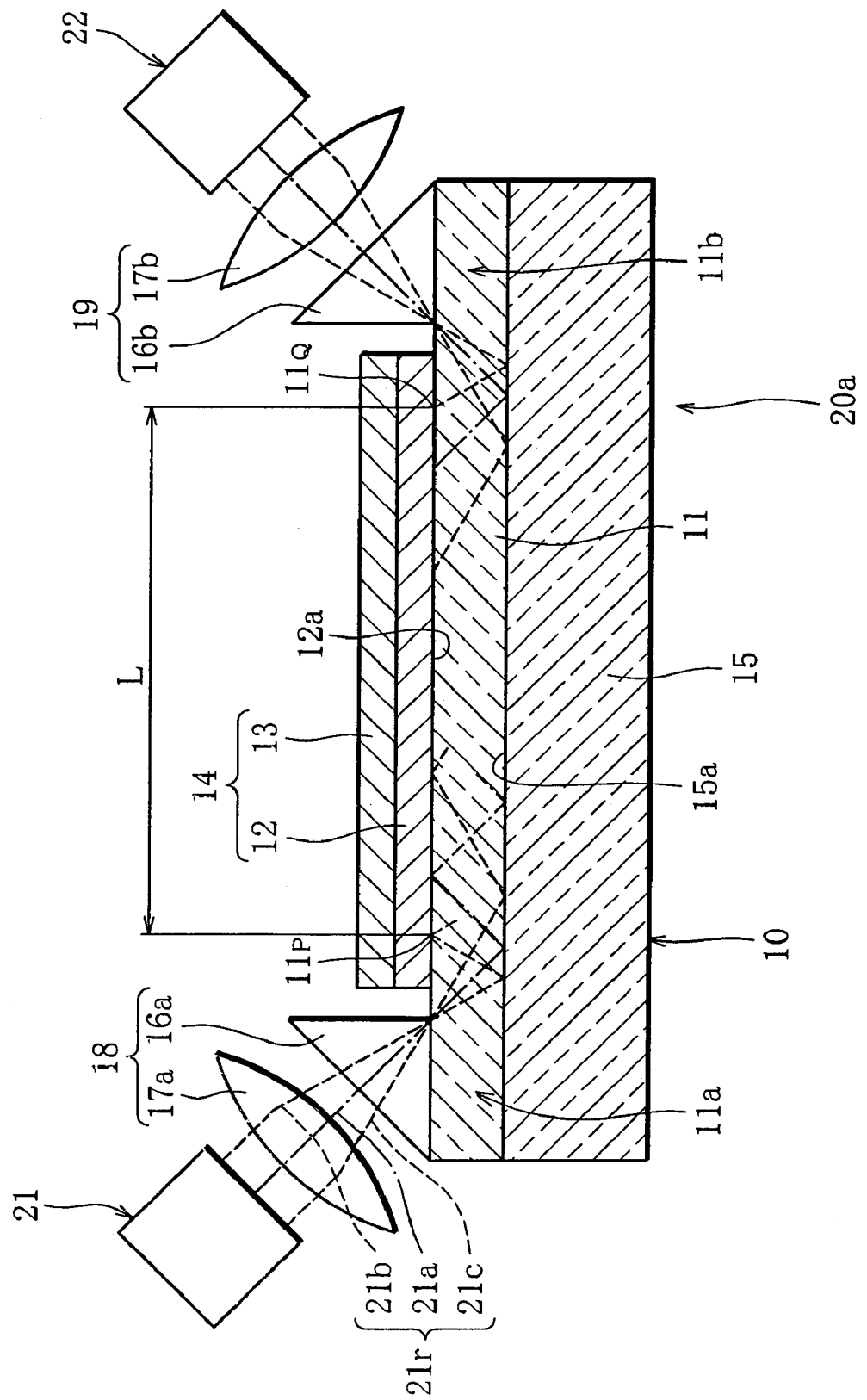
FIG. 1 is a schematic structural diagram showing a hydrogen sensor and a hydrogen gas detecting apparatus according to a first embodiment of the present invention.

Referring to the drawings, hydrogen gas detecting apparatuses according to the present invention will be described.

A hydrogen sensor and a hydrogen gas detecting apparatus according to a first embodiment of the present invention will be described on the basis of FIGS. 1 and 2. Components having the same functions as those of the conventional hydrogen sensor are assigned the same reference characters.

FIG. 1 is a schematic structural diagram showing a hydrogen sensor 10 and a hydrogen gas detecting apparatus 20a.

The hydrogen sensor 10 includes a thin film layer 12 formed on a top surface of a core 11, and a catalyst layer 13 formed on a top surface of the thin film layer 12. The thin film layer 12 and the catalyst layer 13 constitute a light control film 14. The bottom surface of the core 11 is in contact with a cladding 15. The core 11 (planar optical transmission medium) and the cladding 15 (substrate) constitute a slab optical waveguide. A first interface 12a is created between the top surface of the core 11 and the thin film layer 12, and a second interface 15a is created between the bottom surface of the core 11 and the cladding 15.

A prism 16a is bonded to the top surface of the core 11 at an end portion, which will be called a first end portion 11a, to form an entrance section 18 together with a lens 17a introducing light into the prism 16a. A prism 16b is bonded to the top surface of the core 11 at the opposite end portion, which will be called a second end portion 11b, to form an exit light-collecting section 19 together with a lens 17b collecting light exiting the prism 16b.

The thin film layer 12 can be formed by sputtering, vacuum evaporation, electron beam evaporation, plating or the like. The composition of the thin film layer 12 is MgNix ($0 \leq x < 0.6$), for example, and the thickness thereof is between 1 nm and 100 nm, for example. The catalyst layer 13 can be formed by coating the top surface of the thin film layer 12 with palladium. The thickness of the catalyst layer 13 is between 1 nm and 100 nm, for example. The composition, etc. of the thin film layer 12 and the catalyst layer 13 are not limited to the aforementioned, but can be modified variously as necessary.

The hydrogen gas detecting apparatus 20a includes a light source 21 and an optical sensor 22, in addition to the hydrogen sensor 10 configured as described above.

Light emitted from the light source 21 includes a ray 21a traveling along the optical axis of the light source 21 to enter the entrance section 18 and rays traveling along optical paths other than the optical axis to enter the entrance section 18. In FIG. 1, the ray following the optical path upwardly furthest from the optical axis to enter the entrance section 18 is indicated as a ray 21b, while the ray following the optical path downwardly furthest from the optical axis to enter the entrance section 18 is indicated as a ray 21c. All the rays emitted from the light source 21, including the rays 21a, 21b and 21c, are indicated as light 21r. The light rays after entering the entrance section 18 are indicated in like manner.

The light 21r converges through the lens 17a and enters the prism 16a, then converges to a point on the top surface of the first end portion 11a of the core 11 and enters the core 1. After entering the core 1, the light 21r spreads in the direction of thickness of the core 11, which means that the rays 21a, 21b, 21c enter the core 11 at different incident angles. Consequently, as shown in FIG. 1, the rays 21a, 21b, 21c are transmitted inside the core 11 to the second end portion 11b by being reflected by the first and second interfaces 12a and 15a alternately, where, due to their different incident angles, the rays 21a, 21b, 21c are reflected by the first interface at different points on a line L extending in the direction of length of the core 11 (line connecting points 11p and 11q in FIG. 1). Then, after exiting from the top surface of the second end portion 11b of the core, the rays 21a, 21b, 21c are collected by the exit light-collecting section 19 composed of the prism 16a and the lens 17b, and transmitted to the optical sensor 22.

Since the reflection of the light 21r by the first interface 12a occurs on the line L extending in the direction of length of the core 11, the hydrogen gas detecting apparatus 20a can detect a change in reflectance of the first interface 12a that has happened in any part of the aforementioned line L. Consequently, the hydrogen gas detecting apparatus 20a can detect hydrogen gas with high sensitivity and improved reliability.

Alternatively, the entrance section 18 may include, for example a means for spreading light 21r in the direction of width of the core 11 (lenticular lens, Fresnel lens or the like, for example), when the light 21r enters the core through the top surface of the first end portion 11a of the core along the length of the core 11. As indicated by a chain line and two broken lines in FIG. 2, when the light 21r spread only in the direction of width W, not in the direction of thickness of the core 11 on its entering the core 11 (rays 21d and 21e are those at the opposite ends of the spread light), the optical path of the light 21r is indicated only in chain line in FIG. 1.

Figure 2:
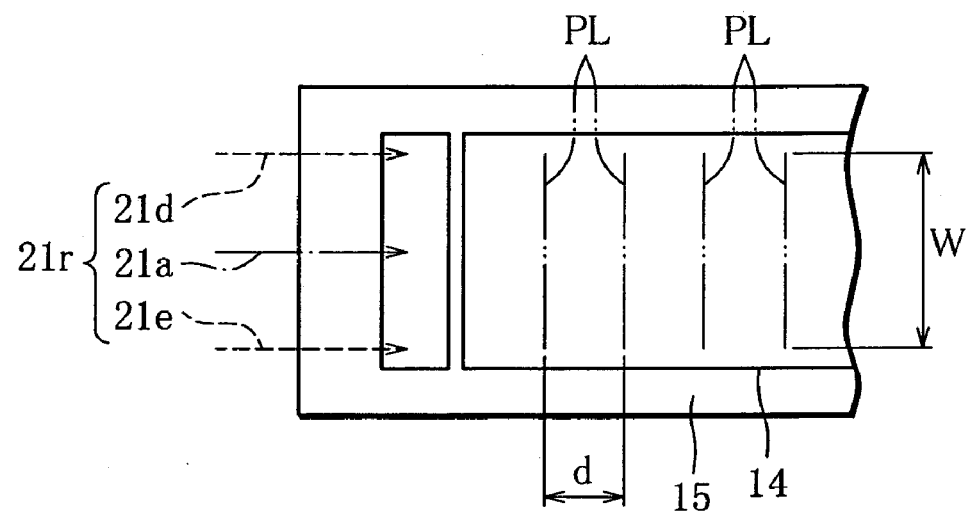
FIG. 2 is a schematic plan view showing a periphery of an entrance section including the entrance section of the hydrogen sensor of FIG. 1.
Figure 3:
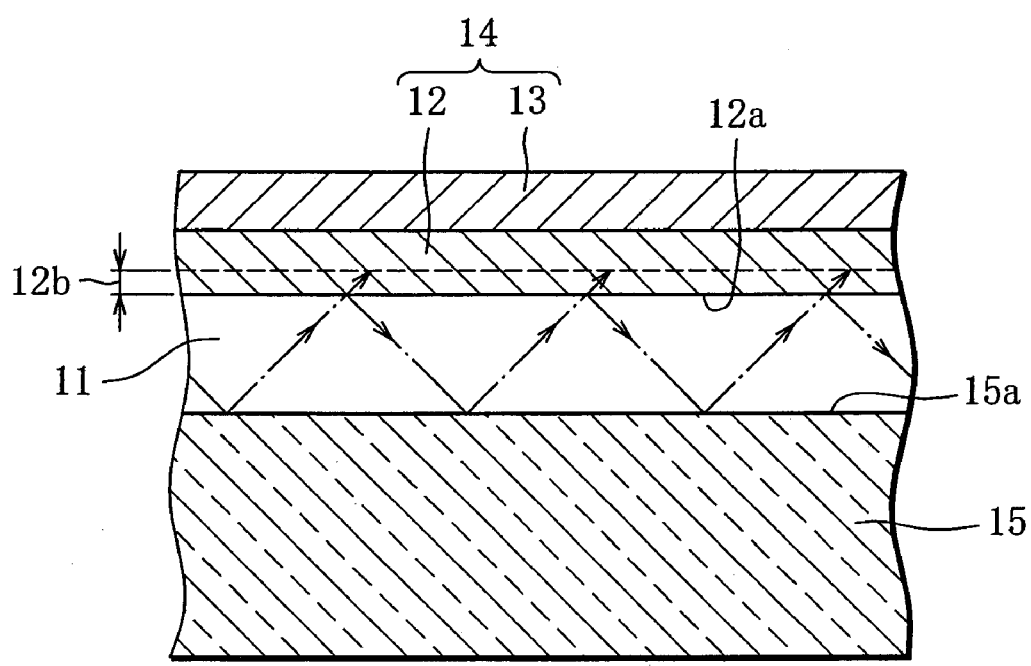
FIG. 3 is a schematic structural diagram showing a cross-section of an optical transmission medium of the hydrogen sensor of FIG. 1.

Thus, as shown in FIG. 2, the light 21r is transmitted inside the core 11 to the second end portion 11b by being reflected by the first and second interfaces 12a and 15a alternately, where the reflection of the light 21r by the first interface occurs on lines PL located at equal intervals d in the direction of length of the core 11. Then, after exiting from the second end portion 11b, the light 21r is collected by the exit light-collecting section 19 and transmitted to the optical sensor 22. Thus, the hydrogen gas detecting apparatus 20a can detect a change in reflectance of the first interface 12a that has happened in any part of any of the aforementioned lines PL. Consequently, the hydrogen gas detecting apparatus 20a can detect hydrogen gas with high sensitivity and improved reliability.

If the hydrogen sensor 10 is configured such that light 21r is spread in both the thickness and width directions of the core 11 when the light 21r enters the core through the top surface of the first end portion 11a of the core, the light 21a is transmitted inside the core 11 to the second end portion 11b by being reflected by the first and second interfaces 12a and 15a alternately, where the reflection of the light 21a by the first interface occurs on a rectangular plane of length L and width W parallel to the length and width of the core 11. Then, after exiting from the second end portion 11b, the light 21a is collected by the exit light-collecting section 19 and transmitted to the optical sensor 22. Thus, the hydrogen gas detecting apparatus 20a can detect a change in reflectance of the first interface 12a that has occurred in any part of the aforementioned rectangular plane. Consequently, the hydrogen gas detecting apparatus 20a can detect hydrogen gas with higher sensitivity and more improved reliability.

As described above, the hydrogen sensor 10 and hydrogen gas detecting apparatus 20a comprise the entrance section 18 including a means for spreading light 21r emitted from the light source 21 in the direction of thickness of the core 11 and/or a means for spreading light 21r from the light source 21 in the direction of width of the core 11, on its entering the core 11, whereby realizing high hydrogen-gas sensitivity.

Further, in the above-described hydrogen sensor 10 and hydrogen gas detecting apparatus 20a, hydrogenation of the thin film layer 12 is detected from the light 21r transmitted inside the core 11 in a manner confined between the first and second interfaces 12a and 15a. Consequently, hydrogen gas can be detected without being affected by disturbance light, dust in the atmosphere or the like.

Next, a hydrogen sensor and a hydrogen gas detecting apparatus according to a second embodiment of the present invention will be described on the basis of FIGS. 3 to 6. Components having the same functions as those of the first embodiment will be assigned the same reference characters, and the description of such components will be omitted.

In a light control film 14 consisting of a thin film layer 12 of magnesium-nickel alloy and a catalyst layer 13 of palladium, when the catalyst layer 13 contacted by hydrogen gas hydrogenates the thin film layer 12, the thin film layer 12 experiences the following state transition: The thin film layer 12 changes from a specular reflection state causing specular reflection of incoming light 21r from the core 11 at the first interface 12a, to an absorption state absorbing the incoming light 21r in its region 12b (see FIG. 3) near the first interface 12a. Then, the thin film layer changes from the absorption state to a transmission state transmitting the incoming light 21r to the catalyst layer 13.

When the thin film layer 12 has changed to the absorption state, part of incoming light 21r on the first interface 12a enters the region 12b of the thin film layer 12, where it is attenuated by being absorbed in the thin film layer 12. The other part of the incoming light 21r on the first interface 12a is reflected from the first interface 12a. Consequently, the amount of light 21r reaching the second end portion 11b of the core 11 reduces.

When the thin film layer 12 has changed to the transmission state, the light 21r is not reflected by the first interface 12a but enters the thin film layer 12, passes through the thin film layer 12 undergoing attenuation, and then passes though the catalyst layer 13, thus leaving the hydrogen sensor 10. Consequently, the amount of light 21r reaching the second end portion 11b of the core 11 reduces more.

Figure 4:
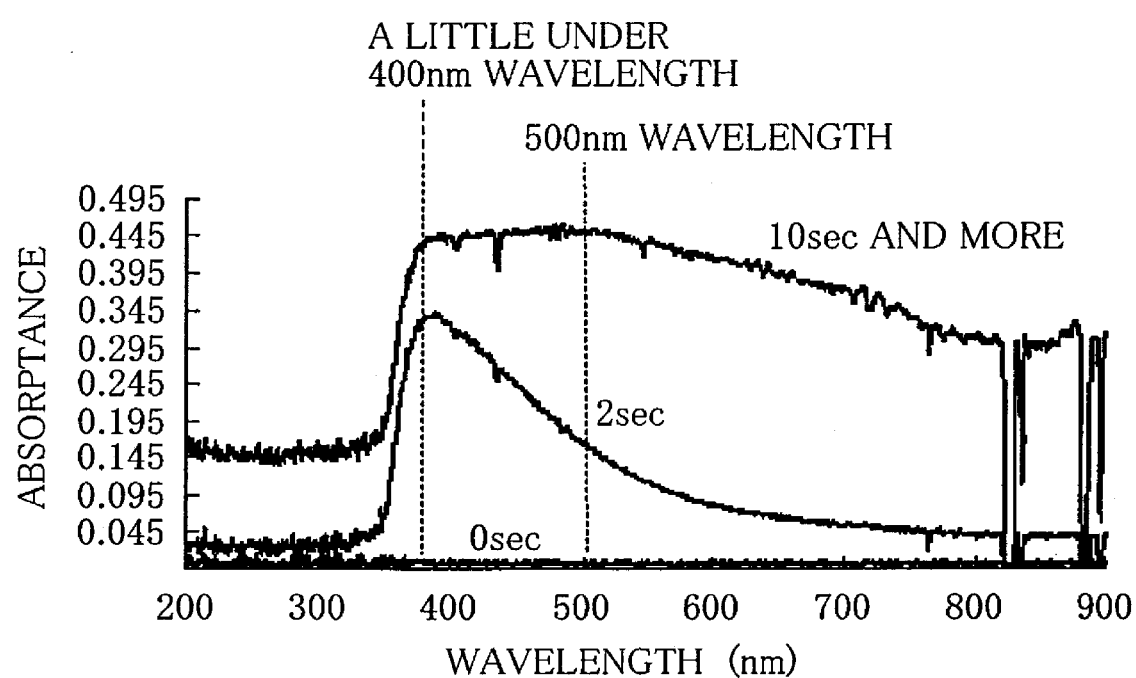
FIG. 4 is a graph showing how the optical absorptance characteristic of a thin film layer varies when a catalyst layer is contacted by hydrogen gas.

FIG. 4 is a graph showing how the optical absorptance characteristic of the light control film 14 varies when the catalyst layer 13 contacted by hydrogen gas causes the transition of the thin film layer 12 from the specular reflection state causing specular reflection of light 21r at the first interface 12a, to the absorption state, and then to the transmission state. When the thin film layer 12 is in the state causing specular reflection of the light 21r at the first interface 12a, the absorptance is zero. When the thin film layer 12 has entered the absorption state, the absorptance starts increasing. Then when the thin film layer 12 has changed to the transmission state, the light 21r passes through the thin film layer 12 and the catalyst layer 13, thus leaking to the outside. FIG. 4 shows absorptance-versus-wavelength characteristics at different times after the catalyst layer 13 is contacted by hydrogen gas, where absorptance of the light control film 14 is plotted on the vertical axis and wavelength of incoming light on the first interface (wavelength in air) is plotted on the horizontal axis.

As seen in FIG. 4, in the case of light having a wavelength of 500 nm, for example, the absorptance reaches approximately 0.145 two seconds after the catalyst layer 13 is contacted by hydrogen gas, and reaches approximately 0.445 ten seconds after the catalyst layer 13 is contacted by hydrogen gas. In the case of light having a wavelength of a little shorter than 400 nm, the absorptance reaches approximately 0.345 two seconds after, and reaches approximately 0.445 ten seconds after. Thus, when only a wavelength range of approximately 400 nm to 500 nm is focused on, the graph shows that, the shorter the wavelength, the shorter time the thin film layer 12 takes to change from the specular reflection state to the transmission state (in other words, the faster the thin film layer 13 responds), so that the absorptance of the light control film 14 increases faster.

As described above, the response of the thin film layer 12 is faster as the wavelength of incoming light is shorter and slower as the wavelength of incoming light is longer (see a wavelength range of a little shorter than 400 nm to 800 nm in the graph of FIG. 4, for example).

Figure 5:
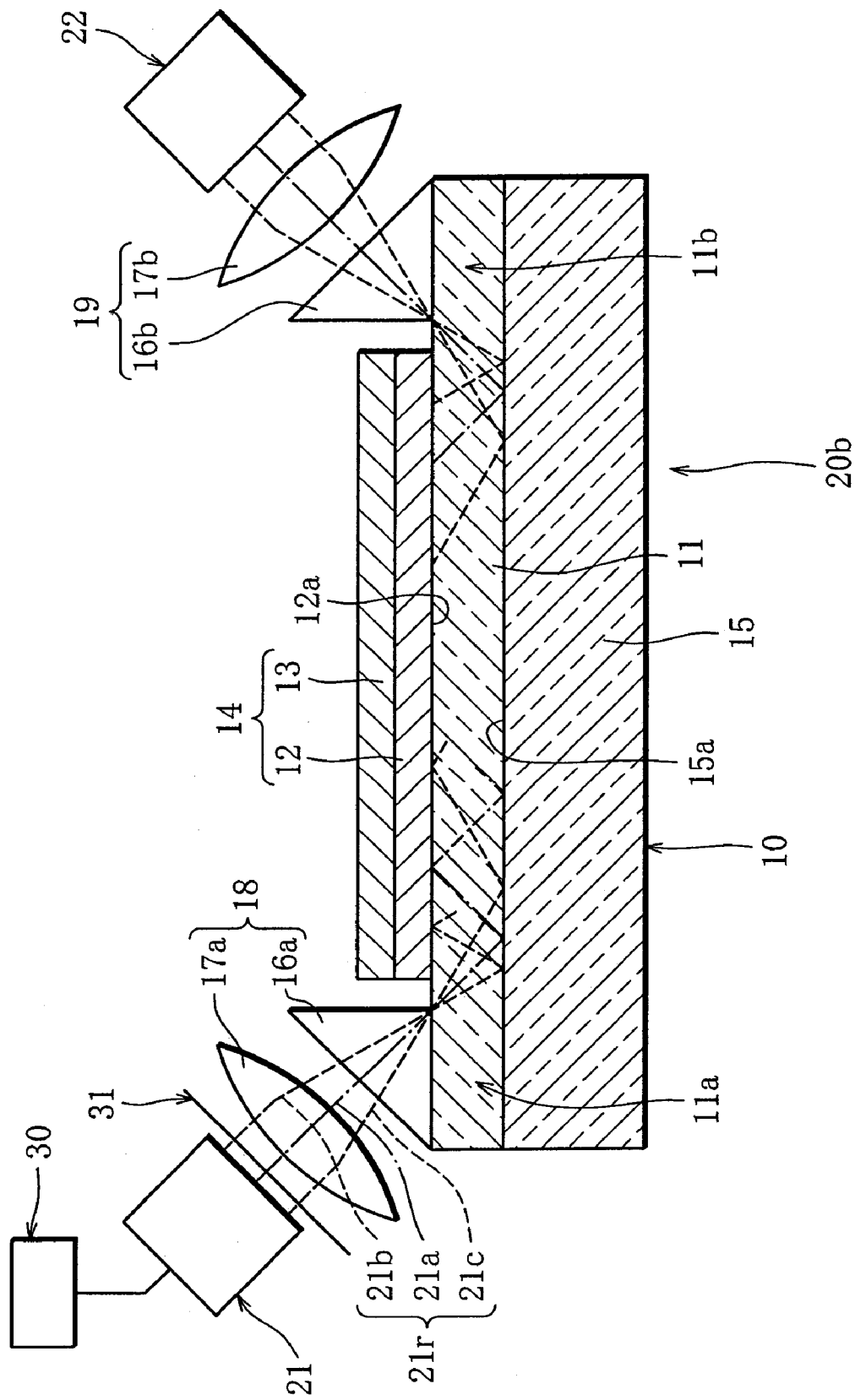
FIG. 5 is a schematic structural diagram showing a hydrogen sensor and a hydrogen gas detecting apparatus according to a second embodiment of the present invention.

FIG. 5 is a schematic structural diagram showing a hydrogen gas detecting apparatus 20b according to a second embodiment of the present invention. A hydrogen sensor 10 is a type in which the time taken for transition from the specular reflection state to the transmission state depends on the wavelength of incoming light on the first interface 12a.

The hydrogen gas detecting apparatus 20b includes a light source 21, a power source 30 and an optical sensor 22 in addition to the hydrogen sensor 10. The light source 21 includes a red LED, a green LED and a blue LED and is configured to emit light with an almost flat wavelength distribution over a wavelength range of 400 nm to 700 nm, for example. The power source 30 can control drive current supplied to the respective LEDs, thereby controlling the wavelength distribution of light 21r emitted from the light source 21. The optical sensor 22 compares the amount of received light with a threshold value optionally set in advance, and detects hydrogen gas from a reduction of the amount of received light below the threshold value.

The color temperature of light 21r emitted from the light source 21 can be changed by manipulating the power source 30 to regulate the emission intensity of the blue, red and green LEDs. For example, increasing the emission intensity of the blue LED while decreasing that of the red and green LEDs results in higher color temperature of light 21r from the light source 21. On the other hand, increasing the emission intensity of the red LED while decreasing that of the blue and green LEDs, for example, results in lower color temperature of light 21r from the light source 21.

Thus, for example when the light source 21r is controlled to emit light 21r with high color temperature, the light 21r transmitted inside the core 11 includes high energy of light emitted by the blue LED (i.e. light having a wavelength from 400 nm to 500 nm, for example). For such light, the thin film layer 13 shows fast response to the catalyst layer 13's contact with hydrogen, so that the absorptance of the light control film 14 increases (thus, the amount of light received by the optical sensor 22 decreases quickly). In this manner, the hydrogen gas detecting apparatus 20b can quickly detect hydrogen gas present in an atmosphere, for example hydrogen gas that has leaked into the atmosphere.

When, on the other hand, the light source 21r is controlled to emit light 21r with low color temperature, the light 21r transmitted inside the core 11 includes high energy of light emitted by the red LED (i.e. light having a wavelength over about 600 nm, for example). For such light, the response of the thin film layer 13 is slow (thus, the amount of light received by the optical sensor 22 slowly decreases), compared with the aforementioned light with high color temperature.

By setting the wavelength distribution of light 21r transmitted inside the core 11 in this manner, the time taken for the transition of the thin film layer 12 from the specular reflection state to the transmission state, therefore, the time taken for reduction in the amount of light received by the optical sensor 22 can be changed. Consequently, the time taken for the optical sensor 22 to detect hydrogen gas can be set by setting the wavelength distribution in addition to the setting of the aforementioned threshold value for the optical sensor 22.

Figure 6A:
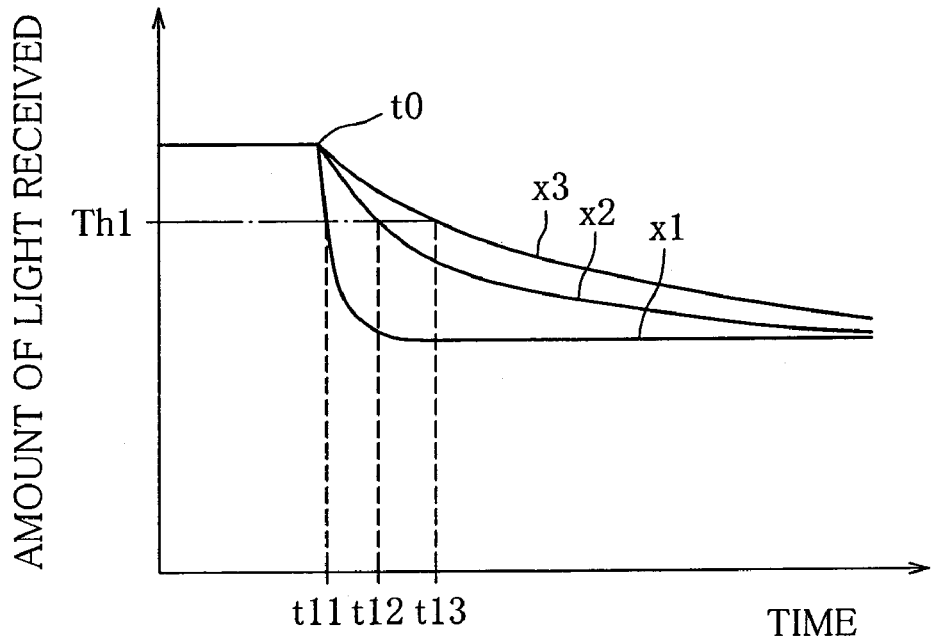
FIG. 6A is a graph showing a relationship between response characteristic of a thin film layer and time taken for detection of hydrogen gas.
Figure 6B:
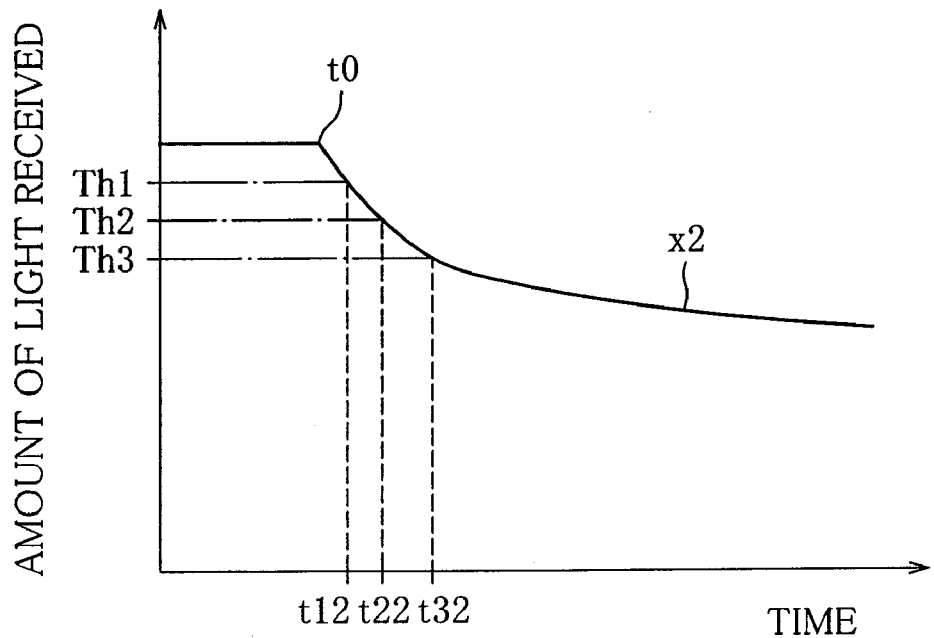
FIG. 6B is a graph showing a relationship between threshold value set for an optical sensor and time taken for detection of hydrogen gas.

FIG. 6A is a graph showing a relationship between response characteristic of the thin film layer and time taken for detection of hydrogen gas, where hydrogen gas is supposed to contact the catalyst layer of the hydrogen sensor 10 at time t0. Faster to slower response characteristics of the thin film layer 12 are shown as response characteristics x1, x2 and x3. FIG. 6B is a graph showing a relationship between threshold value set for the optical sensor 22 and time taken for detection of hydrogen gas, where hydrogen gas is supposed to contact the catalyst layer of the hydrogen sensor 10 at time t0. In FIGS. 6A and 6B, the amount of light received by the optical sensor 22 is plotted on the vertical axis and time is plotted on the horizontal axis.

FIG. 6A shows a relationship between response characteristic and time taken for detection of hydrogen gas, where the threshold value is set to Th1. For the response characteristic x1, for example, time t11 at the point of intersection of the response characteristic x1 with the line of the threshold value Th1 represents the time at which hydrogen gas is detected. The time at the point of intersection of the response characteristic x2 with the line of the threshold value Th1 is t12, and the time at the point of intersection of the response characteristic x3 with the line of the threshold value Th1 is t13 (t11<t12<t13). For the respective response characteristics, times taken for detection of hydrogen gas are t11-t0, t12-t0 and t13-t0, respectively. Thus, slower response of the thin film layer 12 results in later detection of hydrogen gas.

FIG. 6B shows times t12, t22 and t32 at which hydrogen gas is detected when the threshold value is varied among values Th1, Th2 and Th3 (Th1>Th2>Th3), where the response characteristic of the thin film layer 12 is x2. For the respective threshold values, times taken for detection of hydrogen gas are t12-t0, t22-t0 and t23-t0, respectively. Thus, higher threshold value results in earlier detection of hydrogen gas, or in other words, lower threshold value results in later detection of hydrogen gas. In this manner, the hydrogen gas detecting apparatus 20b can quickly detect hydrogen gas present in the atmosphere, for example hydrogen gas that has leaked to the atmosphere, and the time taken for detection of hydrogen gas can be optionally set.

Here, the hydrogen gas detecting apparatus 20b may include a color filter 31 disposed between the light source 21 and the entrance section 18. When the color filter 31 allows light in a wavelength region from 400 nm to 500 nm included in the light 21r emitted from the light source 21 to enter the core 11, the thin film layer 12 shows fast response to the catalyst layer 13 contacted by hydrogen, so that the hydrogen gas detecting apparatus 20b can quickly detect hydrogen gas. When, on the other hand, the color filter 31 allows light in a wavelength region over 600 nm to enter the core 11, the response of the thin film layer 12 is slow. On this principle, the hydrogen gas detecting apparatus 20b allows optional setting of time taken for detection of hydrogen gas.

The location of the color filter 31 is not limited to between the light source 21 and the entrance section 18. For example, the color filter 31 may be arranged at any position between the entrance section 18 and the exit light-collecting section 19 or between the exit light-collecting section 19 and the optical sensor 22. In the hydrogen gas detecting apparatus 20b having such configuration, the color filter 31 can limit the light transmitted to the optical sensor 22 to light in a wavelength region for which the thin film layer 12 shows quick response (quick hydrogenation), or light in a region for which the thin film layer 12 shows slow response (slow hydrogenation).

The hydrogen gas detecting apparatus 20b may be provided with another type of the optical sensor 22 in which a photoelectric transducer having a wavelength-dependent photoelectric conversion characteristic receives light 21r from the exit light-collecting section 22. In such hydrogen gas detecting apparatus 20b, by selecting a suitable photoelectric conversion characteristic to detect light having a wavelength for which the thin film layer 12 is hydrogenated quickly, the hydrogen gas detecting apparatus 22 can detect hydrogen gas quickly. On the other hand, by selecting a suitable photoelectric conversion characteristic to detect light having a wavelength for which the thin film layer 12 is hydrogenated slowly, the hydrogen gas detecting apparatus 22 can detect hydrogen gas slowly.

In the above-described first and second embodiments, the core 11 and the cladding 15 constitute a slab optical waveguide. The optical waveguide is however not limited to the slab optical waveguide. Next, a hydrogen sensor and a hydrogen gas detecting apparatus using an optical waveguide other than the slab optical waveguide will be described.

Figure 7:
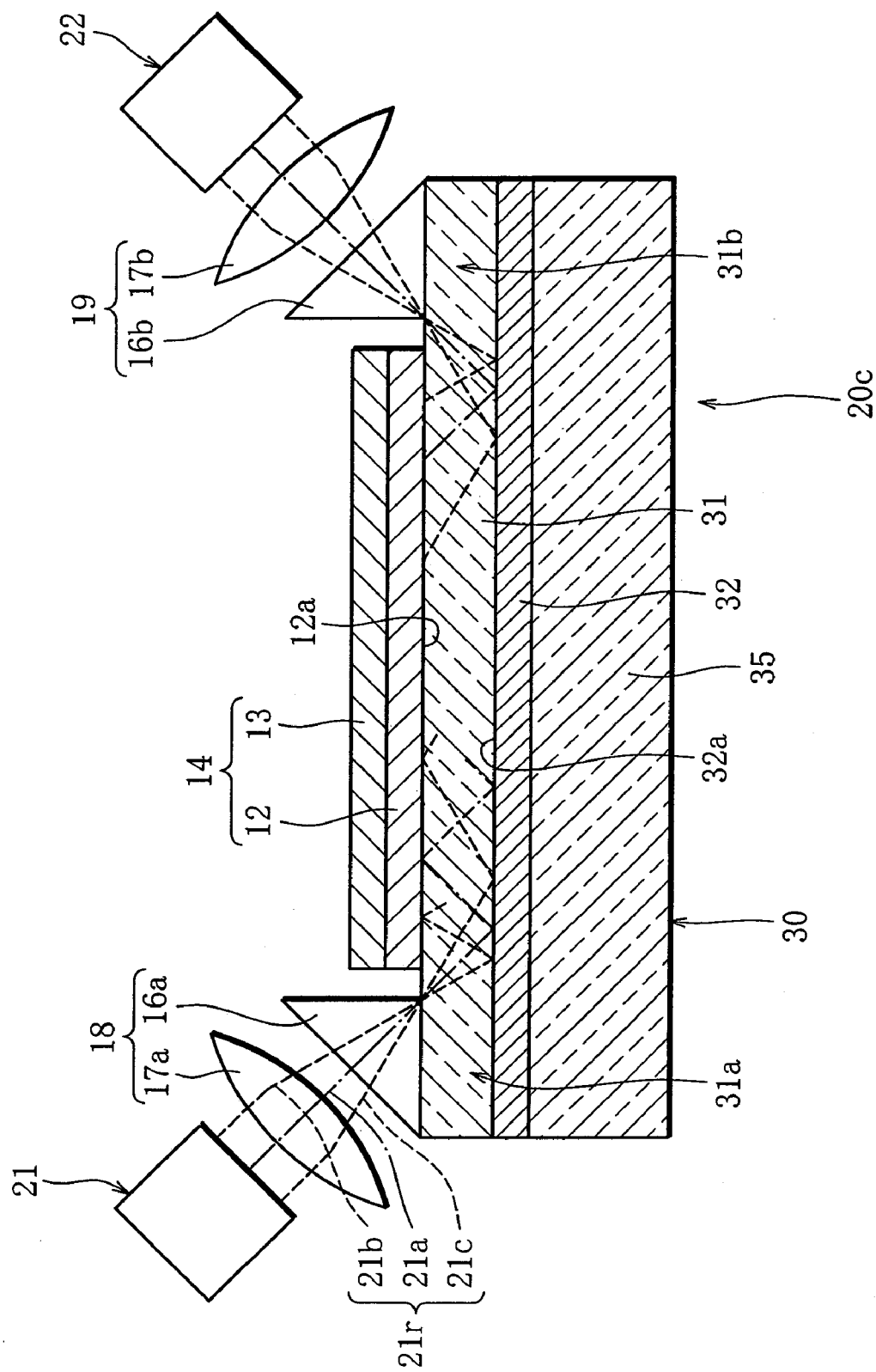
FIG. 7 is a schematic structural diagram showing a hydrogen sensor and a hydrogen gas detecting apparatus according to a third embodiment of the present invention.
Figure 8:
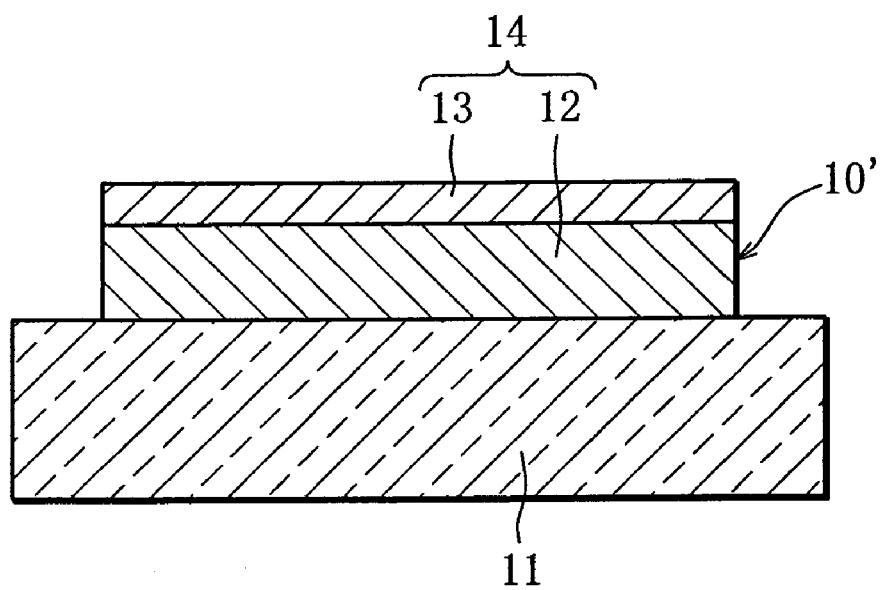
FIG. 8 is a schematic structural diagram showing a conventional hydrogen sensor.
Figure 9:
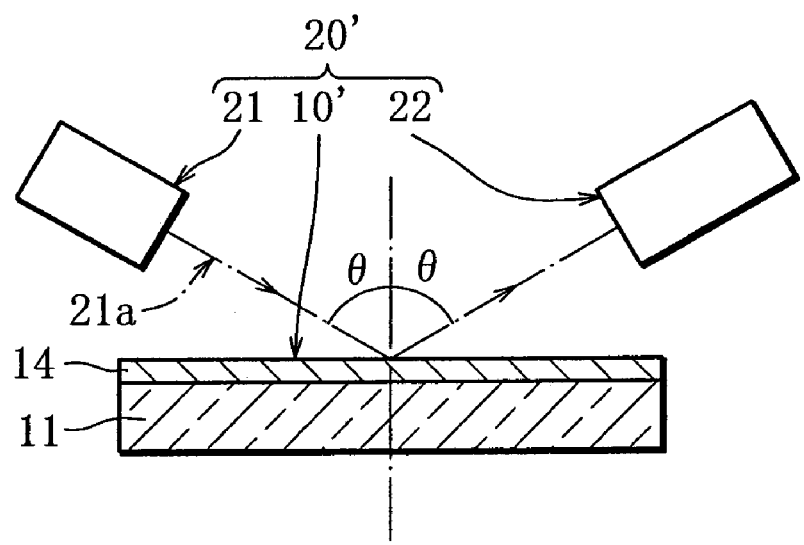
FIG. 9 is a schematic structural diagram showing a conventional hydrogen gas detecting apparatus using the hydrogen sensor of FIG. 8.

FIG. 7 is a schematic structural diagram showing a hydrogen gas detecting apparatus 20c according to a third embodiment of the present invention. The hydrogen gas detecting apparatus 20c includes a light source 21 and an optical sensor 22 both similar to those of the first embodiment. The detailed description of the light source 21 and the optical sensor 21 will therefore be omitted. The hydrogen gas detecting apparatus 20c includes a hydrogen sensor 30 partly different in structure from that of the first embodiment.

Although having an optical waveguide different from that of the first embodiment, the hydrogen sensor 30 is practically the same in structure as the first embodiment, except for the optical waveguide. In the following description, the same components as those of the first embodiment will be assigned the same reference characters and the detailed description thereof will be omitted.

As shown in FIG. 7, like the first embodiment, the hydrogen sensor 30 includes a thin film layer 12 formed on a top surface of a core 31 of $SiO_2$ and a catalyst layer 13 formed on a top surface of the thin film layer 12. As in the first embodiment, the thin film layer 12 and the catalyst layer 13 constitute a light control film 14, and a first interface 12a is created between the top surface of the core 11 and the thin film layer 12. A glass substrate 35 with a reflective film 32 of nickel formed on a top surface thereof is joined to the bottom surface of the core 31, with the reflective film 32 interposed therebetween, so that a second interface 32a is created between the bottom surface of the core 31 and the reflective film 32. Thus, in the hydrogen sensor 30, the core 31 and the reflective film 32 constitute an optical waveguide.

As in the first embodiment, a prism 16a is bonded to the top surface of the core 31 at an end portion, which will be called a first end portion 13a, to form an entrance section 18 together with a lens 17a introducing light into the prism 16a. As in the first embodiment, a prism 16b is bonded to the top surface of the core 31 at the opposite end portion, which will be called a second end portion 31b, to form an exit light-collecting section 19 together with a lens 17b collecting light exiting the prism 16b.

As in the first embodiment, light 21r from the light source enters the core 31 from the first end portion 31a, and inside the core 31, it is reflected by the first and second interfaces 12a and 32a alternately. As in the first embodiment, the light 21r transmitted to the second end portion 31b exits from the second end portion 31b and is transmitted to the optical sensor 22. Thus, like the first embodiment, the hydrogen gas detecting apparatus 20c can detect a change in reflectance of the first interface 12*a*, thereby detecting hydrogen gas with high sensitivity and improved reliability. Further, as in the first embodiment, hydrogenation of the thin film layer 12 is detected from light 21*r* transmitted inside the core 31, which enables detection of hydrogen gas without being affected by disturbance light, dust in the atmosphere or the like.

Further, in the hydrogen gas detecting apparatus 20*c*, the reflective film 32 of nickel forms the second interface 32*a*, which allows practically total internal reflection of the light 21*r* from the secondary interface 32*a*. Since the stable reflection by the second interface 32*a* is established in this manner, the light 21*r* accurately representing a change in reflectance of the first interface 12*a* can be transmitted to the optical sensor 22. Consequently, the hydrogen gas detecting apparatus 20*c* can detect hydrogen gas with improved accuracy. Further, the core 31 of $SiO_2$ and the reflective film 32 of nickel serve as oxidation protection layers for the light control film 14, which leads to improved reliability and durability of the hydrogen sensor 30.

The material for the reflective film 32 is not limited to nickel. For example, the reflective film 32 may be formed of chrome. Also in this case, beneficial effects similar to those mentioned with respect to the third embodiment can be obtained.

Further, the reflective film 32 may be formed of a material that has a refractive index different from that of the core 31 and can transmit light so as to cause specular reflection of light at the second interface 32*a*. In this case, beneficial effects similar to those mentioned with respect to the first embodiment can be obtained, although the above-mentioned excellent effect of total internal reflection of light cannot be obtained.

The material for the core 31 is not limited to $SiO_2$. For example, the core 31 may be formed of glass, acrylate resin, polyethylene or the like.

As understood from the above, the hydrogen gas detecting apparatus 20*c* according to the third embodiment is composed by replacing the hydrogen sensor 10 of the hydrogen gas detecting apparatus 20*a* according to the first embodiment with the hydrogen sensor 30. In like manner, the hydrogen sensor 10 of the hydrogen gas detecting apparatus 20*a* according to the second embodiment may be replaced with the hydrogen sensor 30. In this case, the beneficial effect that the total internal reflection by the second interface 32*a* enables more accurate detection of hydrogen gas is obtained in addition to the above-mentioned beneficial effects of the second embodiment. Also the core 31 and the reflective film 32 serve as oxidation protection layers for the light control film 14 and therefore the beneficial effect that reliability and durability of the hydrogen sensor 30 can be improved is obtained.

In the above, the present invention has been described in detail. The present invention is however not limited to the described embodiments, but can be modified appropriately, without departing from the spirit and scope of the present invention.

For example, the composition, thickness, etc. of the thin film layer and the catalyst layer are not limited to those in the described embodiments but can be modified variously without departing from the scope of the present invention.

Further, for example a light transmission means such as an optical fiber may be provided between the light source and the entrance section of the hydrogen sensor so that light emitted from the light source is transmitted to the entrance section of the hydrogen sensor via the light transmission means. Alternatively, a light transmission means such as an optical fiber may be provided between the exit light-collecting section of the hydrogen sensor and the optical sensor so that light is transmitted from the exit light-collecting section of the hydrogen sensor to the optical sensor via the light transmission means. In this case, in addition to the light transmission means such as an optical fiber, another hydrogen sensor may be provided between the exit light-collecting section of the hydrogen sensor and the optical sensor so that the hydrogen gas detecting apparatus has more than one hydrogen sensor.

Further, for example, the prism and lens constituting the entrance section may be replaced by a glycerin drop and an optical fiber set on the core, respectively. In this case, the optical fiber is inserted directly in the glycerin drop, and light enters the core through the optical fiber.

The invention claimed is:

1. A hydrogen sensor, comprising:
   a planar optical transmission medium;
   a thin film layer formed on a top surface of the planar optical transmission medium to create a first interface between the thin film layer and the planar optical transmission medium;
   a catalyst layer formed on a top surface of the thin film layer;
   a substrate joined to a bottom surface of the planar optical transmission medium to create a second interface between the substrate and the planar optical transmission medium;
   an entrance section for introducing light emitted from a light source into a first end portion of the planer optical transmission medium; and
   an exit light-collecting section for collecting and transmitting the light that is introduced into the first end portion, transmitted inside the planer optical transmission medium and exits from a second end portion of the planar optical transmission medium, to an optical sensor, wherein
   said entrance section includes means for spreading the light emitted from the light source in the direction of thickness of the planar optical transmission medium and introducing the light into the planar optical transmission medium, and/or means for spreading the light emitted from the light source in the direction of width of the planar optical transmission medium and introducing the light into the planar optical transmission medium;
   said planar optical transmission medium transmits the light introduced into the first end portion, by causing it to be reflected by the first and second interfaces alternately; and
   said catalyst layer hydrogenates the thin film layer, when contacted by hydrogen gas present in an atmosphere, and thereby reversibly changes optical reflectance of the thin film layer and the first interface.

2. The hydrogen sensor according to claim 1, wherein said planar optical transmission medium and said substrate constitute a slab optical waveguide allowing light to enter and exit at an angle not limited to a specific angle.

3. The hydrogen sensor according to claim 1, wherein said substrate has a reflective film formed on a top surface thereof and is joined to the bottom surface of the planar optical transmission medium with the reflective film interposed therebetween so that said second interface is created between the planar optical transmission medium and a top surface of the reflective film.

4. The hydrogen sensor according to claim 3, wherein said reflective film is formed of nickel.

5. The hydrogen sensor according to claim 1, wherein when the catalyst layer contacted by hydrogen gas hydrogenates the thin film layer, the thin film layer changes from a specular reflection state causing specular reflection of incoming light at the first interface, to an absorption state absorbing the incoming light in its region near the first interface, and then to a transmission state transmitting the incoming light to the catalyst layer, wherein time taken for the transition of the thin film layer from the specular reflection state to the transmission state depends on a wavelength of incoming light on the first interface.

6. The hydrogen sensor according to claim 5, wherein said catalyst layer is formed of palladium, and said thin film layer is formed of magnesium-nickel alloy.

7. A hydrogen gas detecting apparatus comprising a light source, a hydrogen sensor and an optical sensor, designed for detecting hydrogen gas in an atmosphere by introducing light emitted from the light source into the hydrogen sensor and then detecting light exiting the hydrogen sensor by the optical sensor, wherein the hydrogen sensor comprises:

a planar optical transmission medium;

a thin film layer formed on a top surface of the planar optical transmission medium to create a first interface between the thin film layer and the planar optical transmission medium;

a catalyst layer formed on a top surface of the thin film layer;

a substrate joined to a bottom surface of the planar optical transmission medium to create a second interface between the substrate and the planar optical transmission medium;

an entrance section for introducing light emitted from the light source into a first end portion of the planer optical transmission medium; and an exit light-collecting section for collecting and transmitting the light that is introduced into the first end portion, transmitted inside the planer optical transmission medium and exits from a second end portion of the planar optical transmission medium, to an optical sensor, wherein said entrance section includes means for spreading the light emitted from the light source in the direction of thickness of the planar optical transmission medium and introducing the light into the planar optical transmission medium, and/or means for spreading the light emitted from the light source in the direction of width of the planar optical transmission medium and introducing the light into the planar optical transmission medium;

said planar optical transmission medium transmits the light introduced into the first end portion, by causing it to be reflected by the first and second interfaces alternately; and said catalyst layer hydrogenates the thin film layer, when contacted by hydrogen gas present in an atmosphere, and thereby reversibly changes optical reflectance of the thin film layer and the first interface.

8. The hydrogen gas detecting apparatus according to claim 7, wherein said planar optical transmission medium and said substrate constitute a slab optical waveguide allowing light to enter and exit at an angle not limited to a specific angle.

9. The hydrogen gas detecting apparatus according to claim 7, wherein said substrate has a reflective film formed on a top surface thereof and is joined to the bottom surface of the planar optical transmission medium with the reflective film interposed therebetween so that said second interface is created between the planar optical transmission medium and a top surface of the reflective film.

10. The hydrogen gas detecting apparatus according to claim 9, wherein said reflective film is formed of nickel.

11. The hydrogen gas detecting apparatus according to claim 7, wherein when said catalyst layer contacted by hydrogen gas hydrogenates the thin film layer, the thin film layer changes from a specular reflection state causing specular reflection of incoming light at the first interface, to an absorption state absorbing the incoming light in its region near the first interface, and then to a transmission state transmitting the incoming light to the catalyst layer;

time taken for the transition of the thin film layer from the specular reflection state to the transmission state depends on a wavelength of incoming light on the first interface;

said optical sensor detects hydrogen gas by comparing an amount of the light transmitted from the hydrogen sensor and received by said optical sensor, with a threshold value set in advance; and the hydrogen gas detecting apparatus further comprises at least one of means for changing wavelength distribution of light emitted from the light source, a color filter disposed on an optical path from the light source to the optical sensor and an optical sensor that is configured, as said optical sensor, with a photoelectric transducer having a wavelength-dependent photoelectric conversion characteristic.

12. The hydrogen sensor according to claim 11, wherein said catalyst layer is formed of palladium, and said thin film layer is formed of magnesium-nickel alloy.

\* \* \* \* \*